(12) United States Patent
Paolini et al.

(10) Patent No.: US 7,041,122 B2
(45) Date of Patent: May 9, 2006

(54) INFLATABLE BLANKET WITH A TIE

(75) Inventors: Raymond P. Paolini, Orchard Park, NY (US); Joel T. Jusiak, Holland, NY (US)

(73) Assignee: Gaymar Industries, Inc., Orchard Park, NY (US)

( * ) Notice: Subject to any disclaimer, the term of this patent is extended or adjusted under 35 U.S.C. 154(b) by 0 days.

(21) Appl. No.: 10/728,410

(22) Filed: Dec. 5, 2003

(65) Prior Publication Data

US 2005/0125048 A1 Jun. 9, 2005

(51) Int. Cl.
*A61F 7/00* (2006.01)

(52) U.S. Cl. ...................... 607/107; 607/114

(58) Field of Classification Search ............ 607/104, 607/107, 108–112, 114; 601/148, 150; 602/13, 602/27; 62/259.3; 5/423
See application file for complete search history.

(56) References Cited

U.S. PATENT DOCUMENTS

| 222,690 A | 12/1879 | Goldschmidt |
|---|---|---|
| 1,399,095 A | 12/1921 | Webb |
| 1,777,982 A | 10/1930 | Popp |
| 2,093,834 A | 9/1937 | Gaugler |
| 2,110,022 A | 3/1938 | Kliesrath |
| 2,122,964 A | 7/1938 | Sweetland |
| 2,512,559 A | 6/1950 | Williams |
| 2,601,189 A | 6/1952 | Wales |
| 2,706,988 A | 4/1955 | Weber |
| 3,243,827 A | 4/1966 | Kintner |
| 3,418,726 A | 12/1968 | Sparks |
| 3,610,251 A | 10/1971 | Sanderson |
| 3,610,323 A | 10/1971 | Troyer |
| 3,691,646 A | 9/1972 | Ruffolo |
| 3,714,947 A | 2/1973 | Hardy |
| 3,757,366 A | 9/1973 | Sacher |
| 4,572,188 A | 2/1986 | Augustine et al. |
| 4,660,388 A | 4/1987 | Greene et al. |
| 4,715,070 A | 12/1987 | Montijo |
| 4,777,802 A | 10/1988 | Feher |
| 4,807,644 A | 2/1989 | Sandhaus |
| 4,867,230 A | 9/1989 | Voss |
| 5,125,238 A | 6/1992 | Ragan et al. |
| 5,184,612 A | 2/1993 | Augustine |
| 5,251,347 A | 10/1993 | Hopper et al. |
| 5,300,100 A | 4/1994 | Hickle et al. |
| 5,300,101 A | 4/1994 | Augustine et al. |
| 5,300,102 A | 4/1994 | Augustine et al. |

(Continued)

*Primary Examiner*—Roy D. Gibson
(74) *Attorney, Agent, or Firm*—Roach Brown McCarthy & Gruber; Kevin D. McCarthy

(57) ABSTRACT

The present invention is directed to at least one tie strap positioned on an inflatable blanket. These tie straps, when being used with the blanket, are positioned not on the non-inflatable periphery sections of the inflatable blanket, but on non-periphery sections, like an inflatable section, of the inflatable blanket. This is being done to provide the desired control of the blanket's movement and, if desired, the inflation of the blanket in certain areas of the inflatable blanket. Controlling the inflation of the blanket is obtained by the present straps ability to alter the size of at least a portion of an inflatable chamber within the inflatable blanket. The present ties also provide greater movement control because the tie straps provide desired pressure to at least one section of the inflatable blanket. The tie straps of the present invention are also an integral part of the blanket which means supplemental materials, like tape or ropes, are not needed to control the blanket with the present invention.

6 Claims, 4 Drawing Sheets

U.S. PATENT DOCUMENTS

| | | |
|---|---|---|
| 5,324,320 A | 6/1994 | Augustine et al. |
| 5,336,250 A | 8/1994 | Augustine |
| 5,343,579 A | 9/1994 | Dickerhoff et al. |
| 5,350,417 A | 9/1994 | Augustine |
| 5,360,439 A | 11/1994 | Dickerhoff et al. |
| 5,384,924 A | 1/1995 | Dickerhoff et al. |
| 5,405,370 A | 4/1995 | Irani |
| 5,405,371 A | 4/1995 | Augustine et al. |
| 5,443,488 A | 8/1995 | Namenye et al. |
| 5,447,531 A | 9/1995 | Wood |
| 5,486,207 A | 1/1996 | Mahawili |
| 5,514,169 A | 5/1996 | Dickerhoff et al. |
| 5,545,194 A | 8/1996 | Augustine |
| 5,620,482 A | 4/1997 | Augustine et al. |
| 5,634,889 A * | 6/1997 | Gardner et al. ............. 601/151 |
| 5,735,890 A | 4/1998 | Kappel et al. |
| 5,773,275 A | 6/1998 | Anderson et al. |
| 6,036,722 A * | 3/2000 | Augustine .................... 607/104 |
| 6,241,756 B1 | 6/2001 | Kappel |
| 6,290,716 B1 | 9/2001 | Augustine |
| 6,309,409 B1 | 10/2001 | Anderson et al. |
| 6,719,711 B1 * | 4/2004 | Islava .......................... 602/13 |
| 2002/0043054 A1 * | 4/2002 | Gatto .......................... 54/79.4 |
| 2005/0107856 A1 * | 5/2005 | Gammons ................... 607/104 |

\* cited by examiner

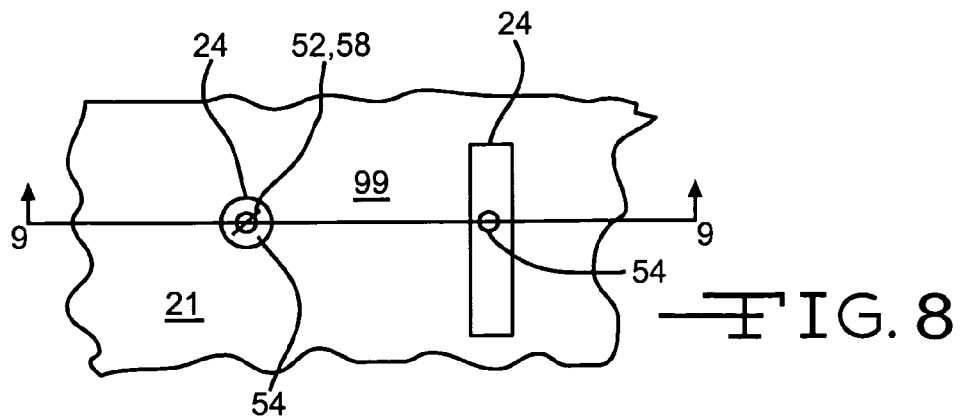
FIG. 8
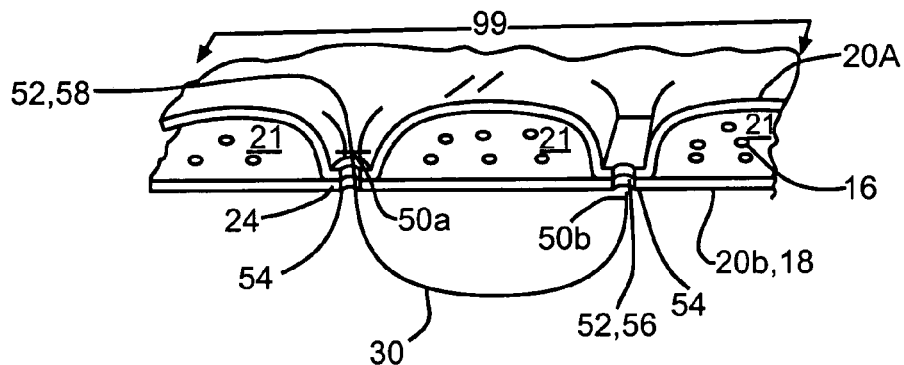
FIG. 9
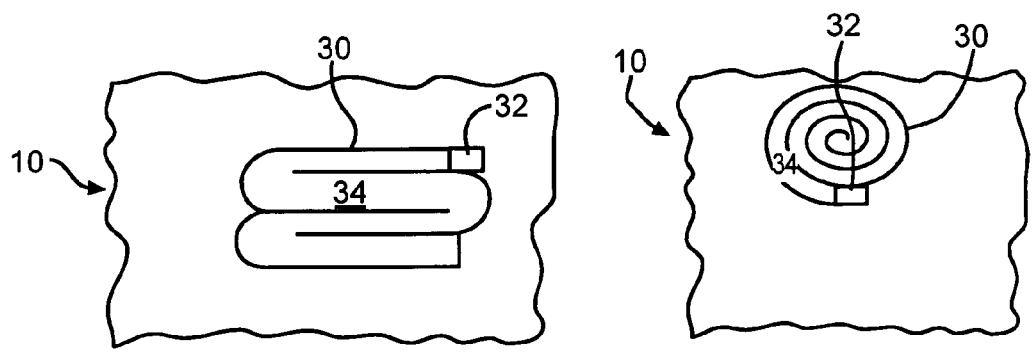
FIG. 10
FIG. 11

INFLATABLE BLANKET WITH A TIE

FIELD OF THE INVENTION

The present invention is directed to inflatable blankets having at least one tie and/or strap thereon.

BACKGROUND OF THE INVENTION

Gaymar Industries, Inc. is the assignee of the present application, and has been manufacturing, selling and offering to sell inflatable blankets for a number of years. On Jun. 8, 1999, Circuit Judge Rader wrote a court decision that described Gaymar's thermal blankets. That decision can be found at 181 F.3d 1291, 1304, 50 USPQ2d 1900, 1909 (Fed. Cir. 1999) and it clearly describes the differences between Gaymar's thermal blanket and at least one competitor's. In his outstanding decision, he wrote, "Convective thermal blankets inflate to direct warm (or cool) air onto a person. Surgeons often use these blankets during and after an operation to prevent or treat hypothermia caused by surgical conditions. Hypothermia results when a patient's body temperature drops below a certain threshold. Surgery often presents the threat of hypothermia. A patient's body temperature may drop significantly during surgery because anesthesia prevents the patient's body from regulating its own temperature. Additionally, operating rooms—kept cool to accommodate the surgeon's working conditions and to reduce the spread of germs—can chill patients. Moreover, surgery often calls for administration of cool intravenous fluids at a time when the patient's body cavity is open.

A convective thermal blanket over the patient is thus necessary to prevent or treat hypothermia during and after surgery. Heated air from a warming unit inflates the blanket. Once inflated, the blanket directs heated air onto the patient through small holes (or "exit ports") in the undersurface of the blanket. With careful use, a convective blanket regulates patient temperature and prevents hypothermia"[, or in some cases hyperthermia.

Gaymar has been manufacturing such blankets] that feature an inflatable quilt-like structure. These blankets attach two sheets of the same amount of flexible, lightweight material around their periphery and at various spots along their surfaces [sometimes referred to as welds or spot welds depending on the shape of the attachment]. In operation, heated air flows onto a patient's body from holes in the undersurface of the blanket, and the blankets do not form a self-supporting or Quonset hut-like structure. Instead, [Gaymar's] blankets lie flat when inflated on a flat surface and rest substantially on a patient when in use." (Bracketed material is added or substitutes terms to make it relevant for this application.)

"It is known that various embodiments of known inflatable thermal blankets have used strips of adhesive tape to prevent a blanket moving with respect to a patient. The adhesive strips may also be used to help control the flow of the thermally controlled air, e.g., to ensure even distribution of the temperature controlled air, or to prevent migration of the air toward a care site. Typically, the adhesive strips adhere the thermal blanket to the patient or to a nearby piece of equipment, such as a hospital bed or operating table. In any such applications, adhesive strips have performed satisfactorily." See U.S. Pat. No. 5,773,275, col. 1, lines 51–60.

In the '275 patent, it is disclosed, and claimed, that a thermal blanket can have "multiple ties connected at separate positions near the periphery to secure the thermal blanket in place." See claim 14. Each of these multiple ties is described as "a flexible elastic or non-elastic strap connected to a flap by adhesive, sewing, stapling, looping through an aperture in the flap and attachment to itself." The opposing ties are secured with (1) buckle, (2) tying them into a knot, or (3) connectors positioned at the respective ties' distal ends. The connectors may be small adhesive patches, snaps, claps (sic), complementary sections of hook and eye material, or another suitable device for connecting the ties. See col. 4, line 48 to col. 5, line 15. The term "flap" is defined as "non-inflated portions of the thermal blanket . . . present along the periphery of the thermal blanket." See col; 3, lines 63–65. Those definitions and descriptions clearly provide notice that the '275 patent has clearly limited the location of straps or ties on a thermal blanket to the non-inflated, periphery portion of the thermal blanket.

Applicants are also aware of U.S. Pat. No. 5,735,890. In the '890 patent, an inflatable blanket having fastening means is disclosed. The fastening means are positioned "along at least one edge of [a] center line seal [which is interconnected with the non-inflated periphery zone of the inflatable blanket], which allow the portions of the blanket, separated by the center line seal, to be held together when it is desired to cover the patient completely. The fastening means may be of any suitable form, such as tie straps, hook and loop fasteners, buttons, snaps, zippers, adhesives, tape, etc." See col. 2, line 66 to col. 3, line 6. In other words, the fastening means is again connected to a non-inflated and an extension of the periphery portion of the inflatable blanket.

Having tie straps, or fastening means, positioned exclusively to the non-inflated periphery portions are easier to manufacture. That may explain why the '890 patent and the '275 patent limit the positions of the ties straps to just the non-inflatable periphery portions of thermal blankets. The straps positioned on non-inflatable periphery positions, however, fail to provide desired further control of blanket's movement and inflation. Applicants have solved these problems.

SUMMARY OF THE INVENTION

The present invention is directed to at least one tie strap positioned on an inflatable blanket. These tie straps, when being used with the blanket, are positioned not on the non-inflatable periphery sections of the inflatable blanket, but on non-periphery sections, like an inflatable section, of the inflatable blanket. This is being done to provide the desired control of the blanket's movement and, if desired, the inflation of the blanket in certain areas of the inflatable blanket. Controlling the inflation of the blanket is obtained by the present straps ability to alter the size of at least a portion of an inflatable chamber within the inflatable blanket. The present ties also provide greater movement control because the tie straps provide desired pressure to at least one section of the inflatable blanket. The tie straps of the present invention are also an integral part of the blanket which means supplemental materials, like tape or ropes, are not needed to control the blanket with the present invention.

BRIEF DESCRIPTION OF THE FIGURES

FIG. 8 is top plan view of an alternative embodiment of the present invention.

FIG. 9 is a view of FIG. 8 taken along the lines 9—9.

FIGS. 10 and 11 illustrate alternative embodiments of the present invention.

DETAILED DESCRIPTION OF THE PRESENT INVENTION

Figure 1:
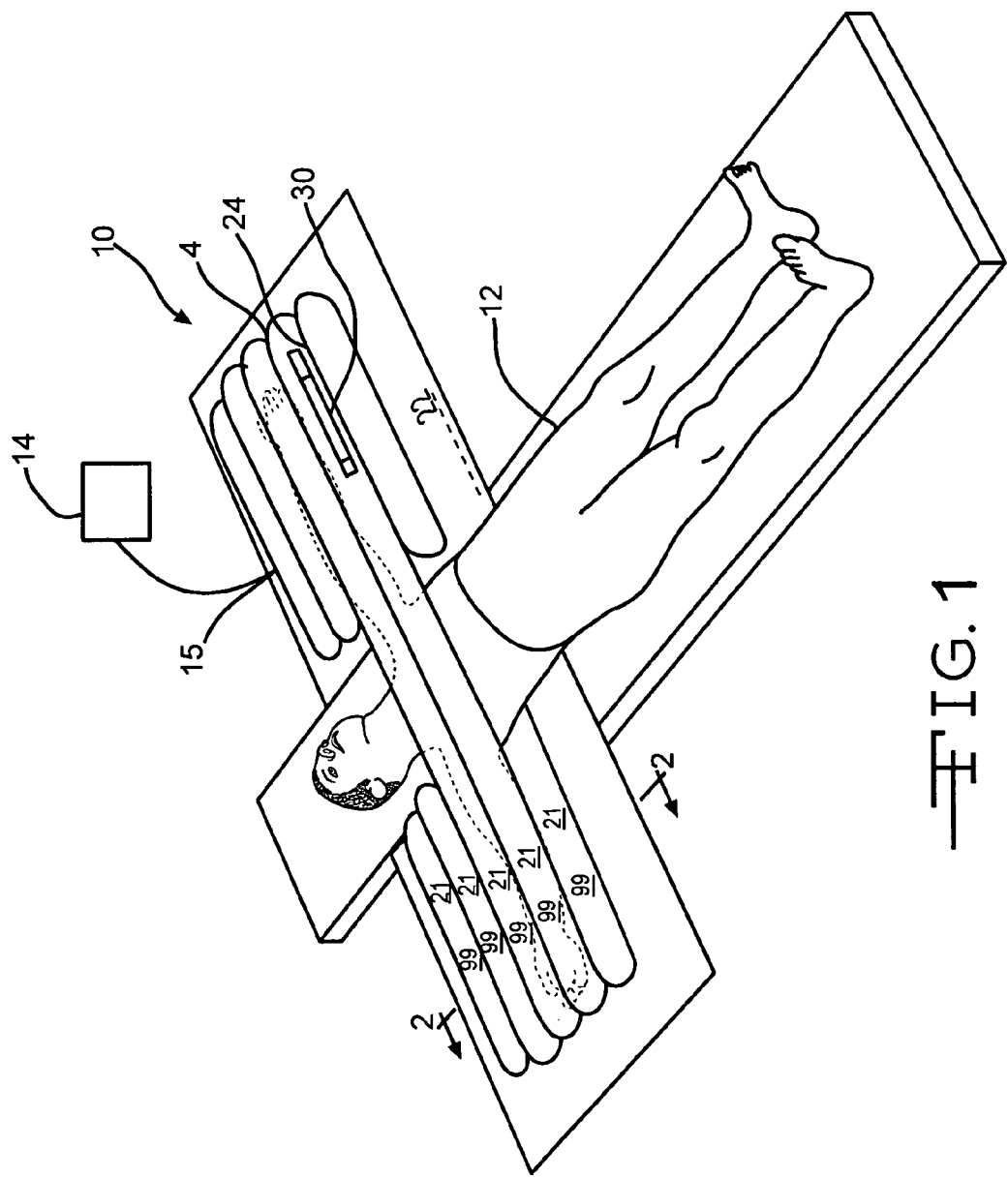
FIG. 1 is a perspective view of the present invention.

Applicant will rely on Judge Rader's description of Gaymar's inflatable thermal blankets, minus ties. A variation of that description is as follows:

Convective thermal blankets 10, as illustrated in FIG. 1, inflate to direct warm (or cool) air onto a person 12. Surgeons often use these blankets 10 during and after an operation to prevent or treat hypothermia caused by surgical conditions or hyperthermia. Hypothermia results when a patient's body temperature drops below a certain threshold, and hyperthermia is just the opposite. Surgery often presents the threat of hypothermia. A patient's body temperature may drop significantly during surgery because anesthesia prevents the patient's body from regulating its own temperature. Additionally, operating rooms—kept cool to accommodate the surgeon's working conditions and to reduce the spread of germs—can chill patients. Moreover, surgery often calls for administration of cool intravenous fluids at a time when the patient's body cavity is open.

Figure 3:
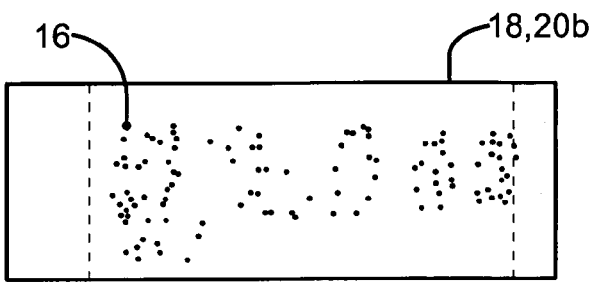
FIG. 3 is a view of FIG. 2 taken along the lines 3—3.

A convective thermal blanket 10 over the patient 12 is thus necessary to prevent or treat hypothermia during and after surgery. Heated air from a warming unit 14, like Gaymar's Medi-Therm unit, inflates the blanket 10 through an inlet 15 of the blanket. Once inflated, the blanket directs heated air onto the patient through small holes 16 (or "exit ports") in the undersurface 18 of the blanket 10 as shown in FIG. 3. With careful use, a convective blanket regulates patient temperature and prevents hypothermia.

Gaymar has been manufacturing such blankets 10 that feature an inflatable quilt-like structure. These blankets, see FIG. 2, attach two sheets 20*a,b* of the same amount of flexible, lightweight material around their periphery 22 and at various spots 24 along their surfaces [sometimes referred to as welds or spot welds depending on the shape of the attachment]. These sheets 20*a,b* and the periphery 22 define at least one inflatable chamber 21 which is the inflatable section 99 of the blanket 10. In operation, heated air flows onto a patient's body from holes 16 in the undersurface 18, 20*b* of the blanket 10, and the blankets 10 do not form a self-supporting or Quonset hut-like structure. Instead, Gaymar's blankets lie flat when inflated on a flat surface and rest substantially on a patient when in use.

Judge Radar's decision did not describe any tie straps on Gaymar's blankets because there were none. Gaymar has reviewed the competitors' inflatable blanket and tie straps. Those tie straps always are an integral part of the periphery 22 and are not designed to be removed there from. The periphery is any part of the blanket 10 that is not (1) inflated and (2) completely surrounded by an inflatable section(s) thereof. These tie straps are designed to connect with other corresponding tie straps from the other side of the periphery. These tie straps do not provide sufficient control of the movement of the blanket 10 while it is inflated. These issues have been resolved by the present invention.

FIRST EMBODIMENT

Figure 2:
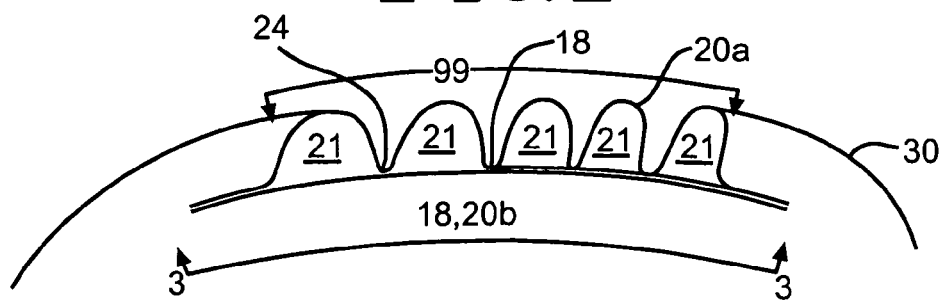
FIG. 2 is a view of FIG. 1 taken along the lines 2—2.

FIG. 2 illustrates a tie strap 30. The tie strap 30 is an elongated piece of material. The material can be the same material as used with the sheet material 20*a,b*, or 20*a* or 20*b* (if different) or similar material. A portion 32 of the strap 30 is designed to be permanently attached to a non-periphery section of the blanket 30.

Figure 4:
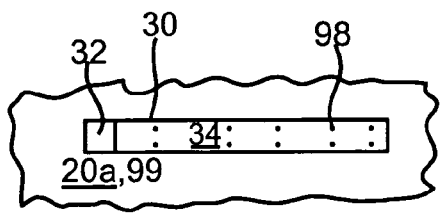
FIG. 4 is an enlarged view of FIG. 1 taken along the box 4.

The attachment portion 32 is sonic welded, heat welded, adhered, stapled, or equivalent thereof to the exterior surface (top surface or bottom surface, preferably the top surface) of the inflated section of the blanket 10. Preferably, the attachment portion 32 is sonic welded or heat welded to the inflated section 99. The remaining portion 34 of the strap 30 is easily removably welded, adhered, stapled, or tacked 98 to the blanket 30 as shown in FIG. 4.

Figure 5:
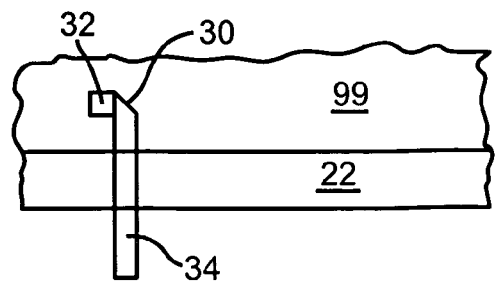
FIG. 5 is an alternative embodiment of FIG. 4.

When the blanket is being positioned on the patient, the remaining portion 34 is released from its removable attachment. The remaining portion is sufficiently long enough that it can go under the patient's table and attach, for example by hook and loop, snaps, adhesive, buckling, knotting, to the top surface or bottom surface, to the attachment portion 32, to the remaining portion adjacent and/or near to the attachment portion 32 as shown in FIGS. 5 and 6, or to a second tie strap which is identical to or a variation, for example any of the other embodiments of the present invention as discussed in greater detail below, of the tie strap 30.

SECOND EMBODIMENT

Figure 6:
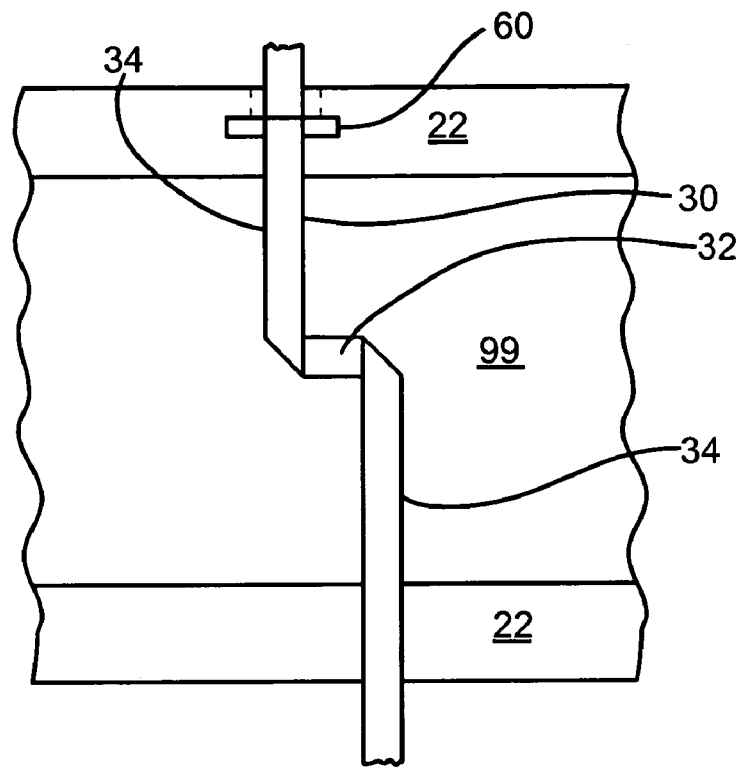
FIG. 6 is an alternative embodiment of FIG. 4.

The second embodiment is similar to the first embodiment except the remaining portion 34 extends in both directions from the attachment surface, as shown in FIG. 6.

THIRD EMBODIMENT

Figure 7:
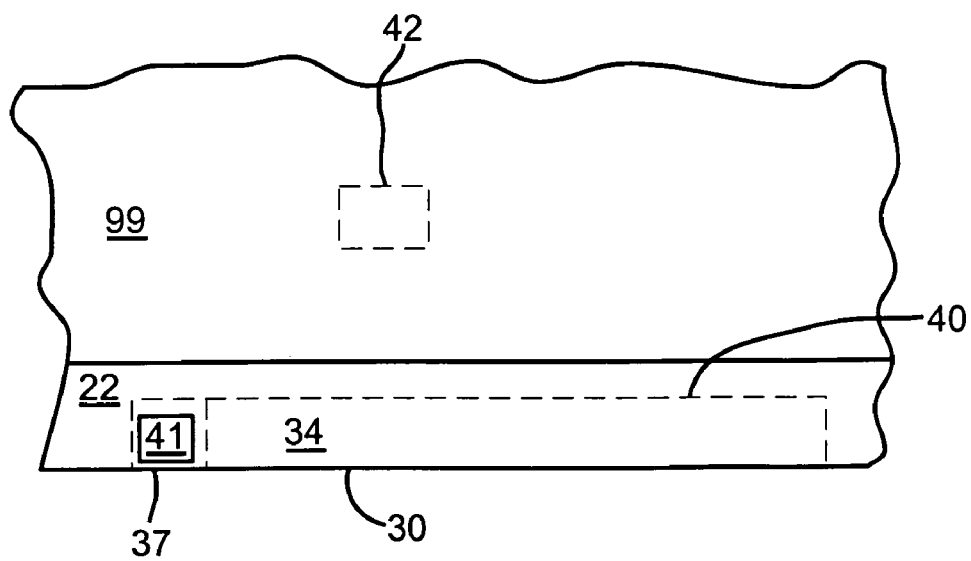
FIG. 7 is an alternative embodiment of the tie strap.

The tie strap 30 is a removable section from the periphery 22 as shown in FIG. 7. By removable, we mean the tie strap 30 is extensively perforated 40 with the periphery 22, and designed to be removed from the periphery when used. The tie strap 30 has an attachment portion 32 and at least one remaining portion. The remaining portion can be designed like the first or second embodiments of the present invention.

The attachment portion 32 will have an adhesive, a hook/loop system 41, or equivalent thereof that attaches to a predetermined portion 42 of the inflatable section, preferably the top surface, of the blanket 10.

FOURTH EMBODIMENT

The tie strap 30 is an elongated member having at least two terminal ends 50*a,b*. Positioned on each terminal end 50 is a needle-like, turnable locking mechanism 52 that is capable of being rotated from a perpendicular position 58 (locking position) to vertical position 56 (insertion position) as illustrated in FIGS. 8 and 9. When the locking mechanism 52 is in a vertical position it can (1) be inserted into an aperture 54 in a spot 24 or (2) form the aperture in the spot 24. Once positioned in the aperture, the turnable locking mechanism 52 is able to be maneuvered to its locking position. The remaining portion of the elongated member is positioned around the table of the patient or the patient's appendage or chest cavity without applying too much pressure to the patient. The remaining portion can be elastic-like material or not,

FIFTH EMBODIMENT

The periphery 22 can have slits 60, as shown in FIG. 6, that receive the tie straps that are attached to the inflatable surface, preferably the top surface, of the blanket 10. These slits ensure that the tie straps 30 are properly positioned for various sized patients. In addition, the slits allow the user of the blanket 10 to obtain further control of the desired inflation of the blanket 10.

SIXTH EMBODIMENT

The tie straps 30 can be shaped like a circular (see FIG. 11) or a rectangular (see FIG. 10) pull-strap when the positioned and attached to the topsurface of the blanket 10. These designs compress the area in which the tie straps 30 are positioned. Such compression is desired when space is limited.

It is appreciated that various modifications to the inventive concepts described herein may be apparent to those of ordinary skill in the art without departing from the scope of the present invention as defined by the herein appended claims.

We claim:

1. An inflatable blanket for covering and bathing a patient in a thermally-controlled inflating medium comprising:
   an inflatable apparatus having (a) a flexible base sheet with a plurality of exhaust ports, (b) a flexible overlaying sheet attached to the base sheet to define at least one inflatable chamber between the base sheet and the overlaying sheet, (c) an inlet port to receive the thermally-controlled inflating medium that can enter the at least one inflatable chamber, (d) a periphery that is uninflatable and not entirely surrounded by the inflatable chamber, and (e) at least two spot welds and each spot weld is capable of having an aperture therein;
   an elongated tie strap having two terminal ends and at each terminal end is a turnable locking mechanism, each turnable locking mechanism is capable of forming the aperture or entering the aperture of one spot weld and being positioned to removably secure the tie strap to the blanket.

2. A method of securing into position an inflatable blanket for covering and bathing a patient in a thermally-controlled inflating medium comprising:
   using an inflatable apparatus having (a) a flexible base sheet with a plurality of exhaust ports, (b) a flexible overlaying sheet attached to the base sheet to define at least one inflatable chamber between the base sheet and the overlaying sheet, (c) an inlet port to receive the thermally-controlled inflating medium that can enter the at least one inflatable chamber, (d) a periphery that is uninflatable and not surrounded by the inflatable chamber, and (e) at least two spot welds and each spot weld is capable of having an aperture therein;
   positioning a tie strap on a non-periphery surface of the inflatable blanket wherein the tie strap is selected from the group consisting of:
   I. an elongated tie strap having (a) an attachment portion that is fixedly attached to the non-periphery surface of the inflatable blanket, and (b) a remaining portion that is removably attached to the non-periphery surface of the inflatable blanket and extends from the attachment portion a sufficient distance to be able secure the inflatable blanket in place,
   II. an elongated tie strap (A) having (a) an attachment portion that is removably attachable to the non-periphery surface of the inflatable blanket, and (b) a remaining portion that extends from the attachment portion a sufficient distance to be able secure the inflatable blanket in place, and (B) prior to being attached for the first time to the non-periphery surface the tie strap is extensively perforated to and extended from the periphery,
   III. an elongated tie strap having two terminal ends and at each terminal end is a turnable locking mechanism, each turnable locking mechanism is capable of forming the aperture or entering the aperture of one spot weld and being positioned to removably secure the tie strap to the blanket, and
   IV. combinations thereof; securing the inflatable blanket in place through the tie straps.

3. The inflatable blanket of claim 2 wherein the periphery has at least one slit to receive at least a portion of the remaining portion of the tie strap.

4. The inflatable blanket of claim 2 wherein the non-periphery surface is selected from the group consisting of the flexible base sheet with a plurality of exhaust ports, the flexible overlaying sheet, and any welded portion that is surrounded by the inflatable chamber.

5. A method of securing into position an inflatable blanket for covering and bathing a patient in a thermally-controlled inflating medium comprising:
   using an inflatable apparatus having (a) a flexible base sheet with a plurality of exhaust ports, (b) a flexible overlaying sheet attached to the base sheet to define at least one inflatable chamber between the base sheet and the overlaying sheet, (c) an inlet port to receive the thermally-controlled inflating medium that can enter the at least one inflatable chamber, and (d) a periphery that is uninflatable and not encircled by the inflatable chamber;
   positioning a tie strap on a non-periphery surface of the inflatable blanket wherein the tie strap is selected from the group consisting of:
   I. an elongated tie strap having (a) an attachment portion that is fixedly attached to the non-periphery surface of the inflatable blanket, and (b) a remaining portion that is removably attached to the non-periphery surface of the inflatable blanket and extends from the attachment portion a sufficient distance to be able secure the inflatable blanket in place,
   II. an elongated tie strap (A) having (a) an attachment portion that is removably attachable to the non-periphery surface of the inflatable blanket, and (b) a remaining portion that extends from the attachment portion a sufficient distance to be able secure the inflatable blanket in place, and (B) prior to being attached for the first time to the non-periphery surface the tie strap is extensively perforated to and extended from the periphery, and
   III. combinations thereof
   securing the inflatable blanket in place through the tie straps;
   wherein the periphery has at least one slit to receive at least a portion of the remaining portion of the tie strap.

6. The inflatable blanket of claim 5 wherein the non-periphery surface is selected from the group consisting of the flexible base sheet with a plurality of exhaust ports, the flexible overlaying sheet, and any welded portion that is entirely surrounded by the inflatable chamber.

* * * * *